United States Patent [19]

Auditore-Hargreaves

[11] Patent Number: 4,473,638

[45] Date of Patent: Sep. 25, 1984

[54] SPECIFIC BINDING ASSAY

[75] Inventor: Karen Auditore-Hargreaves, Wilmington, Del.

[73] Assignee: E. I. Du Pont de Nemours and Company, Wilmington, Del.

[21] Appl. No.: 370,927

[22] Filed: Apr. 22, 1982

[51] Int. Cl.$^3$ .................. G01N 33/54; C12Q 1/26; C12Q 1/54; C12N 9/96
[52] U.S. Cl. .......................................... 435/7; 435/14; 435/25; 435/188
[58] Field of Search ................... 435/4, 7, 188, 810, 435/14, 25

[56] References Cited

U.S. PATENT DOCUMENTS 4,366,243 12/1982 Rupchock .............................. 435/7

Primary Examiner—Esther M. Kepplinger

[57] ABSTRACT

An improvement in a specific binding assay for determining a ligand in a liquid medium, in which assay the labelled conjugate includes FAD and the ligand and in which the labelled conjugate can bind to apoglucose oxidase to form a holoenzyme is provided. The improvement, which renders the assay practical at 37° C., comprises carrying out the assay in the presence of at least about a 250 mM concentration of a polyhydric aldehyde or alcohol, including substrate.

10 Claims, No Drawings

SPECIFIC BINDING ASSAY

FIELD OF THE INVENTION

This invention relates to an improvement in a specific binding assay in which the labelled conjugate includes flavin adenine dinucleotide and a ligand and in which the labelled conjugate can bind to apoglucose oxidase to form a holoenzyme.

BACKGROUND INFORMATION

Hornby et al., U.S. Pat. No. 4,238,565, disclose a specific binding assay for determining a ligand (L) in a liquid medium. In several examples, the labelled conjugate is FAD, which is a prosthetic group residue (Pr), coupled to L through a linking group (R). In such an assay, a known quantity of the labelled conjugate, Pr-R-L, is added to a liquid medium, for example, a blood sample, which contains an unknown quantity of a ligand, for example, theophylline. A known titer of a ligand binding component (B), for example, theophylline antiserum, is also added. B attaches in a competitive reaction to L and Pr-R-L to form L-B and Pr-R-L-B, respectively. Then, a known amount of glucose oxidase apoenzyme (Apo) is added to the medium. The apoenzyme binds to Pr-R-L, forming a holoenzyme, Apo-Pr-R-L, which is an active enzyme. Apo is sterically inhibited, however, from binding to Pr-R-L-B due to the presence of B. Thus, the amount of holoenzyme formed is proportional to the amount of L in the medium.

The amount of holoenzyme glucose oxidase is measured by its activity in the presence of glucose, the enzyme substrate. Glucose is converted through the action of the enzyme, among other products, to hydrogen peroxide which can be measured colorimetrically by known techniques.

Carrico et al., U.S. Pat. No. 4,171,432, disclose a labelled conjugate comprising FAD as the prosthetic group residue and an iodothyronine as the ligand for use in the specific binding assay disclosed in U.S. Pat. No. 4,238,565, issued to Hornby et al.

The above-described specific binding assay is typically carried out at about 25° C. using about 0.1M glucose as substrate for the glucose oxidase. This amount of glucose is about four times the known $K_m$ for glucose oxidase at 25° C., $K_m$ being the substrate concentration at which the rate of enzyme activity is one-half the maximum rate, and is the amount conventionally used in enzyme-enzyme substrate reactions. The assay is accurate, easily carried out and reproducible. However, the assay does not produce quantifiable results when carried out at high temperature, e.g., about 37° C. which is the temperature at which certain automated clinical analyzers operate. Therefore, an improvement which enhances the sensitivity of the assay system at 37° C. is highly desirable.

Dixon et al., "Enzymes," 137-138, Academic Press (1979), state that, in some cases, an enzyme substrate can act as an enzyme activator. A well studied example of activation of an enzyme by a substrate is activation of phenylalanine hydroxylase by phenylalanine as reported as Shiman, J. Biol. Chem., Volume 255, 10029 (1980). Massey et al., J. Biol. Chem., Volume 241, 3417 (1966) postulate that binding of D-amino acid oxidase substrate to the enzyme promotes a conformational rearrangement of the enzyme which is required for full enzyme activity.

SUMMARY OF THE INVENTION

The invention is an improved specific binding assay utilizing a labelled conjugate for determining a ligand in a liquid medium wherein the labelled conjugate includes flavin adenine dinucleotide (FAD) and the ligand and wherein the labelled conjugate can bind to apoglucose oxidase to form a holoenzyme, the improvement comprising carrying out the assay in the presence of at least about a 250 mM concentration of a polyhydric aldehyde or alcohol, which concentration includes a substrate for the holoenzyme, such as glucose.

DETAILED DESCRIPTION OF THE INVENTION

The improvement of the invention pertains to all specific binding assays in which the labelled conjugate includes FAD and a ligand and in which the labelled conjugate can bind to apoglucose oxidase to form a holoenzyme. Such assays are disclosed by Hornby et al., U.S. Pat. No. 4,238,565, which is incorporated herein by reference.

FAD is an organic prosthetic group which, when coupled to certain apoenzymes, forms an active enzyme, or holoenzyme. The apoenzyme and holoenzyme used in the improved process of the invention are, respectively, apoglucose oxidase and glucose oxidase. A ligand is a substance the presence or amount of which in a liquid medium is to be determined. Ligands which can be assayed by the improved process of the invention are those which can be bound to FAD, to form a labelled conjugate, without substantially inhibiting the ability of FAD to form active glucose oxidase when coupled to apoglucose oxidase. Methods for preparing the labelled conjugates are known in the art and are disclosed, for example, in U.S. Pat. Nos. 4,238,565, Hornby et al., and 4,171,432, Carrico et al.

Apoglucose oxidase is unstable at 37° C. in certain solvents. Therefore, the apoenzyme should be maintained in a stabilizing medium, such as a sorbitol solution, or should be kept at about 10° to 25° C. until a few minutes prior to use in an assay.

By polyhydric aldehydes is meant $\alpha$- and $\beta$-anomers of mono- and polysaccharides, preferably mono- and disaccharides, for example, glyceraldehyde, threose, erythrose, ribose, arabinose, xylose, lyxose, allose, altrose, glucose, mannose, gulose, idose, galactose, talose, sucrose, maltose and lactose. Polyhydric alcohols preferably have up to 6 carbon atoms, for example, ethylene glycol, glycerol, tetritols such as erythritol, pentitols such as xylitol and hexitols such as sorbitol.

In accordance with the improvement provided by this invention, the concentration of polyhydric aldehyde or alcohol, including substrate which must be present, is at least about 250 mM. Use of such a high concentration of the aldehyde or alcohol has now been found to increase the sensitivity of the assay at 37° C. The increase in sensitivity can be large enough to render the specific binding assay of this invention practical at 37° C.

The preferred aldehyde or alcohol is glucose. The optimum concentration of glucose, in terms of assay sensitivity enhancement, appears to be greater than about 2000 mM. As a practical matter, however, a 2000 mM glucose solution may be difficult to process in an automated clinical analyzer. The preferred concentration of six-carbon monosaccharides and of disaccharides, including glucose, is at least about 500 mM, more preferably, about 1000 mM. When lower aldehydes or alcohols are used, higher concentrations are desirable. For example, when glycerol is used, the preferred concentration is at least about 2000 mM.

EXAMPLES

The following illustrative examples, in which all percentages are by weight, were carried out using pooled human serum.

EXAMPLE 1

Theophylline Assay in Presence of Glucose

The reagents used in this example, and their final concentrations, were:

| A. theophylline standards | 0 to 4 ng/mL |
|---|---|
| (0, 10, 20 or 40 μg/mL in | |
| 20 μl serum; standards | |
| diluted 1:9 in saline) | |
| B. 4-aminoantipyrene | 0.2 mM |
| horseradish peroxidase | 60 μg/ml |
| apoglucose oxidase | 1600 nM |
| theophylline antiserum | 1/400 dilution |
| C. glucose | 100 to 1000 mM |
| dihydroxybenzene sulfonic acid | 2 mM |
| bovine serum albumin | 1% |
| FAD-theophylline | 60 nM | in a final volume of 560 μl.

The assays were carried out in a Gemsaec centrifugal analyzer at 37° C. in 0.1M phosphate buffer, pH 7.0. The Gemsaec rotor, which contains sixteen radially-extending sets of three wells, was loaded as follows: reagent mixture A in the outermost well, reagent mixture B in the center well and reagent mixture C in the innermost well. Prior to loading, reagent mixtures A and C were equilibrated to 37° C. Reagent mixture B was equilibrated to 37° C. for about 5 minutes prior to each assay. Incubation of reagent mixture B for 30 minutes had been found to result in a loss of activity.

Dihydroxybenzene sulfonic acid, 4-aminoantipyrene and horseradish peroxidase were used to detect hydrogen peroxide. Bovine serum albumin was added because it was thought that it might improve activity; its presence has not been proven to be advantageous.

Enzyme activity was determined by measuring the change in milliabsorbance units per minute, ΔX, at 510 nM. Results are reported in the following table which shows ΔX for each theophylline concentration and each glucose concentration, each reported ΔX being an average of two to five runs.

| Glucose | Theophylline (μg/mL) | | | |
|---|---|---|---|---|
| (mM) | 0 | 10 | 20 | 40 |
| 100 | 70 | 80 | 85 | 100 |
| 250 | 240 | 315 | 340 | 370 |
| 500 | 410 | 570 | 600 | 660 |
| 1000 | 640 | 860 | 900 | 980 |

The results show increasing ΔX (at all theophylline concentrations) with increasing glucose concentration, establishing that the assay becomes a practically useful one at 37° C. when at least about a 250 mM concentration of glucose is used.

EXAMPLE 2

Theophylline Assay in Presence of Glucose, α-/β-Glucose, Glycerol and Sucrose

The procedure was substantially the same as described above in Example 1 except that the theophylline standard solution did not contain theophylline and theophylline antiserum was not used. The concentration of glucose was varied from 0 to 1000 mM and additional aldehydes or alcohols were: mixed α- and β-glucose, glycerol and sucrose. Results are tabulated below. Each reported ΔX is an average of 3 runs. The "Improvement" is the factor by which ΔX, using a 100 mM concentration of glucose alone, was increased by employing the assay of this invention.

| Glucose (mM) | Other Aldehyde or Alcohol (mM) | ΔX | Improvement |
|---|---|---|---|
| 100 | — | 150 | 1 |
| 1000 | — | 1140 | 7.8 |
| 100 | α-/β-Glucose (900) | 1150 | 7.7 |
| 100 | Glycerol (1900) | 390 | 2.6 |
| 100 | Sucrose (525) | 770 | 5.2 |
| 0 | α-/β-Glucose (900) | 1150 | 7.7 |

These results show that a variety of aldehydes and alcohols affords an increase in holoenzyme glucose oxidase activity in the assay of this invention. Use of the β-anomer of glucose does not significantly affect the results.

EXAMPLE 3

Demonstration of Need for Substrate

The procedure of Example 2 was followed, except that ΔX is the average of two to five runs at each condition, with results as follows:

| Glucose (mM) | Other Aldehyde or Alcohol (mM) | ΔX | Improvement |
|---|---|---|---|
| 100 | — | 70 | 1 |
| 1000 | — | 465 | 6.6 |
| 100 | Sucrose (525) | 210 | 3 |
| 100 | Mannitol (990) | 270 | 3.9 |
| 100 | Glycerol (1900) | 150 | 2.1 |
| 0 | Sucrose (525) | 0 | 0 |
| 0 | Mannitol (990) | 0 | 0 |
| 0 | Glycerol (1900) | 0 | 0 |

The results show that sucrose, mannitol, and glycerol do not behave as enzyme substrates which are necessary for carrying out the assay of this invention.

I claim:

1. In a specific binding assay for quantitatively detecting a ligand in a liquid sample, said assay comprising the steps of (1) reacting said liquid sample with a liquid reagent comprising (i) a ligand binding component, (ii) a conjugate comprising flavin adenine dinucleotide and a ligand, (iii) apoglucose oxidase and (iv) a substrate, wherein the conjugate is capable of binding to the apoglucose oxidase to form a holoenzyme which, in turn, is capable of catalyzing the conversion of the substrate into a detectable product; and (2) measuring the detectable product, the improvement comprising carrying out the assay in a liquid solution at about 37° C. in the presence of at least a 250 mM final concentration of a polyhydric aldehyde or polyhydric alcohol, the polyhydric aldehyde or polyhydric alcohol being the same as or different from the substrate, whereby the formation of the holoenzyme from the apoglucose oxidase is provided.

2. The process of claim 1 wherein the ligand is theophylline.

3. The process of claim 1 wherein the polyhydric aldehyde or alcohol is a mono- or disaccharide or is a polyhydric alcohol having up to six carbon atoms.

4. The process of claim 3 wherein the polyhydric aldehyde or alcohol is glucose or sucrose.

5. The process of claim 3 wherein the polyhydric aldehyde or alcohol is a six-carbon monosaccharide or a disaccharide and the concentration thereof is about 1000 mM.

6. The process of claim 5 wherein the polyhydric aldehyde or alcohol is glucose or sucrose.

7. The process of claim 6 wherein the ligand is theophylline.

8. The process of claim 3 wherein the polyhydric aldehyde or alcohol is a six-carbon monosaccharide or a dissacharide and the concentration thereof is at least about 500 mM.

9. The process of claim 8 wherein the polyhydric aldehyde or alcohol is glucose or sucrose.

10. The process of claim 8 wherein the ligand is theophylline.

* * * * *